US008506641B2

(12) United States Patent
Graham et al.

(10) Patent No.: US 8,506,641 B2
(45) Date of Patent: Aug. 13, 2013

(54) ARTHRODESIS IMPLANT FOR FINGER JOINTS AND RELATED METHODS

(75) Inventors: Thomas James Graham, Timonium, MD (US); H. Brent Bamberger Do, Kettering, OH (US); James Howard Calandruccio, Memphis, TN (US); James Higgins, Baltimore, MD (US); Thomas A. Wiedrich, Wilmette, IL (US); Louise M. Focht, Del Mar, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 160 days.

(21) Appl. No.: 12/203,244

(22) Filed: Sep. 3, 2008

(65) Prior Publication Data
US 2010/0057214 A1  Mar. 4, 2010

(51) Int. Cl.
*A61F 2/42* (2006.01)
(52) U.S. Cl.
USPC ..................... 623/21.15; 623/21.11
(58) Field of Classification Search
USPC .................. 623/21.11–21.17; 606/906, 280, 606/71, 281–283, 291, 289
See application file for complete search history.

(56) References Cited

U.S. PATENT DOCUMENTS

| 4,164,793 A | 8/1979 | Swanson | 3/1.91 |
|---|---|---|---|
| 4,198,712 A | 4/1980 | Swanson | 3/1.91 |
| 4,936,860 A | 6/1990 | Swanson | 623/21 |
| 4,969,908 A | 11/1990 | Swanson | 623/21 |
| 5,314,485 A | 5/1994 | Judet | 623/21 |
| 5,326,364 A | 7/1994 | Clift, Jr. et al. | 623/21 |
| 5,360,431 A | 11/1994 | Puno et al. | 606/72 |
| 5,645,605 A | 7/1997 | Klawitter | 623/21 |
| 5,749,872 A * | 5/1998 | Kyle et al. | 606/66 |
| 5,827,285 A | 10/1998 | Bramlet | 606/60 |
| 5,984,926 A | 11/1999 | Jones | 606/72 |
| 5,984,970 A * | 11/1999 | Bramlet | 623/21.15 |
| 6,221,074 B1 | 4/2001 | Cole et al. | 606/62 |
| 6,283,969 B1 | 9/2001 | Grusin et al. | 606/69 |
| 6,284,001 B1 * | 9/2001 | Knapp | 623/21.14 |
| 6,302,887 B1 | 10/2001 | Spranza et al. | 606/73 |

(Continued)

FOREIGN PATENT DOCUMENTS

WO   96/03084   2/1996
WO   01/24717   4/2001

OTHER PUBLICATIONS

TONIER US, Medical Professionals, Wrist Products, CoverLoc Volar Plate, 2008.

(Continued)

*Primary Examiner* — David H Willse
*Assistant Examiner* — Tiffany Shipmon
(74) *Attorney, Agent, or Firm* — Tarolli, Sundheim, Covell & Tummino LLP

(57) ABSTRACT

An arthrodesis implant is for a finger joint of a hand of a patient. The arthrodesis implant may include an extramedullary proximal anchor including a first member having a fastener-receiving passageway therethrough to receive a fastener to anchor the first member to an extramedullary portion of a proximal bone of the finger joint of the hand of the patient. The arthrodesis implant may also include an intramedullary distal anchor having a second member for being anchored within an intramedullary portion of a distal bone of the finger joint of the hand of the patient, and a coupling for securing the first and second members together.

29 Claims, 6 Drawing Sheets

(56) References Cited

U.S. PATENT DOCUMENTS

| | | | |
|---|---|---|---|
| 6,440,135 B2 | 8/2002 | Orbay et al. | 606/69 |
| 6,475,242 B1 | 11/2002 | Bramlet | 623/21.11 |
| 6,565,960 B2 | 5/2003 | Koob et al. | 428/304.4 |
| 6,699,292 B2 | 3/2004 | Ogilvie et al. | 623/21.15 |
| 6,821,530 B2 | 11/2004 | Koob et al. | 424/458 |
| 7,090,676 B2 | 8/2006 | Huebner et al. | 606/71 |
| 7,189,237 B2 | 3/2007 | Huebner | 606/69 |
| 7,326,212 B2 | 2/2008 | Huebner | 606/69 |
| 2004/0138754 A1 | 7/2004 | Lang et al. | 623/20.14 |
| 2004/0158251 A1 | 8/2004 | Morrison et al. | 606/71 |
| 2005/0049710 A1 | 3/2005 | O'Driscoll et al. | 623/20.11 |
| 2005/0070902 A1 | 3/2005 | Medoff | 606/62 |
| 2005/0216090 A1 | 9/2005 | O'Driscoll et al. | 623/20.32 |
| 2005/0234458 A1 | 10/2005 | Huebner | 606/69 |
| 2005/0245931 A1 | 11/2005 | Orbay | 606/69 |
| 2006/0015101 A1 | 1/2006 | Warburton et al. | 606/62 |
| 2006/0089648 A1* | 4/2006 | Masini | 606/69 |
| 2006/0155284 A1 | 7/2006 | Doherty | 606/69 |
| 2006/0173458 A1 | 8/2006 | Forstein et al. | 606/69 |
| 2007/0014649 A1 | 1/2007 | James | 411/81 |
| 2007/0043357 A1 | 2/2007 | Kirschman | 606/61 |
| 2007/0083202 A1 | 4/2007 | Running et al. | 606/62 |
| 2007/0123867 A1 | 5/2007 | Kirschman | 606/61 |
| 2007/0173834 A1 | 7/2007 | Thakkar | 606/62 |
| 2007/0173841 A1 | 7/2007 | Ralph et al. | 606/69 |
| 2007/0265629 A1 | 11/2007 | Martin et al. | 606/69 |
| 2008/0255559 A1* | 10/2008 | Leyden et al. | 606/62 |

OTHER PUBLICATIONS

Anatomi <sup>design</sup>, Ascension® PIP PyroCarbon Total Joint.
SBI Small Bone Innovations, SCS™ Volar Distal Radius Plate Sytem, Surgical Technique, 2006, pp. 1-9.
SBI Small Bone Innovations, SCS™ Volar Distal Radius Plate, 2008.

* cited by examiner

ARTHRODESIS IMPLANT FOR FINGER JOINTS AND RELATED METHODS

FIELD OF THE INVENTION

The present invention relates to the field of arthroplastic implants, and, more particularly, to proximal interphalangeal and metacarpophalangeal joint arthrodesis implants and related methods.

BACKGROUND OF THE INVENTION

The clinical syndrome of Osteoarthritis, which is also known as degenerative arthritis or degenerative joint disease, is characterized by loss of articular cartilage on adjacent bony surfaces resulting in discomfort, loss of motion, and functional impairment. In a similar fashion, inflammatory arthritis, for example, rheumatoid arthritis, results in loss of cartilage surfaces from both biochemical and mechanical means. As the bony surfaces become less protected by cartilage, the patient experiences pain, motion limitation, potential joint instability, and eventual functional loss.

Interphalangeal joint arthritis is the development of Osteoarthritis at a patient's finger joint, for example, the proximal interphalangeal (PIP) joint, i.e. PIP joint arthritis. The PIP joint of the hand is defined by the coupling of the proximal phalanx bone and the middle phalanx bone. Metacarpophalangeal (MCP) joint arthritis is characterized by the development of changes consistent with articular cartilage destruction at the joint between the metacarpal bone and the proximal phalanx bone.

Treatment options for PIP joint and MCP joint arthritis include, for example, splints, i.e. temporary immobilization of the patient's articulating joints, medication, corticosteroid injections, and surgery. Surgical treatments may be generally characterized as "motion-sparing" and "motion-eliminating". Motion-sparing treatments may include, for example, implantation of articulating devices (arthroplasties), and motion-eliminating may include, for example, joint fusion treatments (arthrodesis). For PIP joint arthritis, adjacent portions of the proximal and middle phalanx bones may be replaced. The same is true for the MCP joint, i.e. replacing adjacent portions of the metacarpal and proximal phalanx bones. In both cases, the mobility of the joints is maintained by implantation of biologic or artificial materials that permit the joint to move through an arc of motion, while attempting to relieve pain.

An approach to a motion sparing PIP joint implant is disclosed in U.S. Pat. No. 6,699,292 to Ogilvie et al. The PIP joint implant includes first and second portions, each having mating heads. The mating heads provide a PIP joint prosthesis that may allow smooth articulation.

Another approach to a motion sparing distal interphalangeal (DIP) joint implant is disclosed in U.S. Pat. No. 6,475,242 to Bramlet. The implant includes a pair of screws for securing to the middle and distal phalanges. The implant further includes a flexible connector coupled to the heads of each screw. The flexible connector may comprise a U-shaped bow or a mechanical joint.

A typical approach to motion-eliminating PIP joint or MCP joint arthrodesis includes the tension band method, i.e. simple pinning with a smooth wire or plating with conventional implants. These methods include potential drawbacks, for example, technically-demanding implantation procedure resulting in less than optimum accuracy, potential for subsequent hardware removal due to smooth wire migration or tension band "knot" irritation/abrasion on local tendons, and nonunion (or failure of the two bones to unite at the site of the desired fusion).

SUMMARY OF THE INVENTION

In view of the foregoing background, it is therefore an object of the present invention to provide a finger joint arthrodesis implant that is more effective and readily implanted.

This and other objects, features, and advantages in accordance with the present invention are provided by an arthrodesis implant for a finger joint of a hand of a patient. The arthrodesis implant may include an extramedullary proximal anchor comprising a first member having at least one fastener-receiving passageway therethrough to receive at least one fastener to anchor the first member to an extramedullary portion of a proximal bone of the finger joint of the hand of the patient. The arthrodesis implant also includes an intramedullary distal anchor comprising a second member for being anchored within an intramedullary portion of a distal bone of the finger joint of the hand of the patient, and a coupling for securing the first and second members together. Advantageously, the arthrodesis implant accurately fuses the finger joint of the patient's hand.

More specifically, the coupling may include a tube connected to the first member and extending transversely therefrom, and a fastening arrangement within the tube for securing the first and second members together. The fastening arrangement may also comprise a threaded shaft connected to the second member and extending outwardly therefrom, a threaded sleeve to receive the threaded shaft, and a tool engaging head connected to the threaded sleeve. Furthermore, the tube may have an internal reduced diameter portion defining a stop for the threaded sleeve. For example, the tube may extend transversely from the first elongate member at an angle in a range of 20 to 90 degrees.

In some embodiments, the first member may comprise an elongate curved body. Furthermore, the elongate curved body may have rounded corner portions. The second member may comprise a cylindrical body having a textured surface.

Another aspect is directed to a method for making an arthrodesis implant for a finger joint of a hand of a patient. The method may include forming an extramedullary proximal anchor comprising a first member having at least one fastener-receiving passageway therethrough to receive at least one fastener to anchor the first member to an extramedullary portion of a proximal bone of the finger joint of the hand of the patient. The method may also include forming an intramedullary distal anchor comprising a second member for being anchored within an intramedullary portion of a distal bone of the finger joint of the hand of the patient, and providing a coupling for securing the first and second members together.

Another aspect is directed to a method of implanting an arthrodesis implant for a finger joint of a hand of a patient. The method may include providing the arthrodesis implant. The arthrodesis implant may include an extramedullary proximal anchor comprising a first member having at least one fastener-receiving passageway therethrough to receive at least one fastener to anchor the first member to an extramedullary portion of a proximal bone of the finger joint of the hand of the patient, an intramedullary distal anchor comprising a second member for being anchored within an intramedullary portion of a distal bone of the finger joint of the hand of the patient, and a coupling for securing the first and second members together. The method may also include implanting the extramedullary proximal anchor into the proximal bone, implanting the intramedullary distal anchor into the distal bone, and securing the extramedullary proximal anchor together with the intramedullary distal anchor with the coupling.

DETAILED DESCRIPTION OF THE PREFERRED EMBODIMENTS

Figure 1:
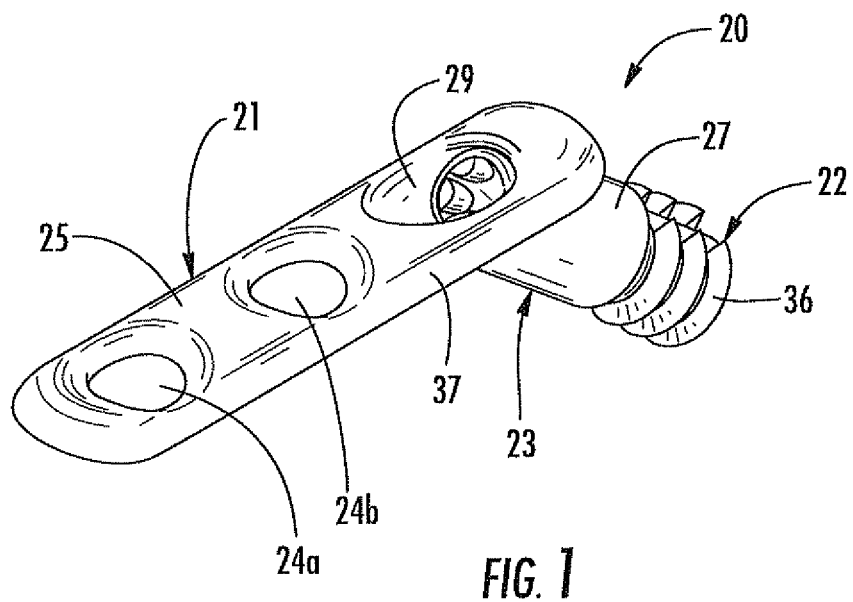
FIG. 1 is a top perspective view of an arthrodesis implant according to the invention.
Figure 2:
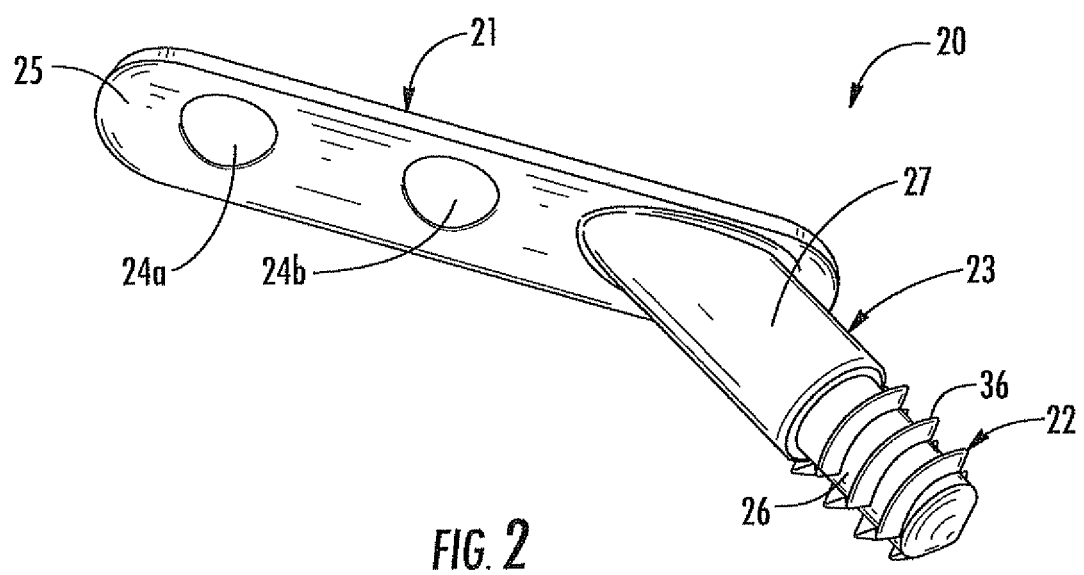
FIG. 2 is a bottom perspective view of the arthrodesis implant of FIG. 1.
Figure 3:
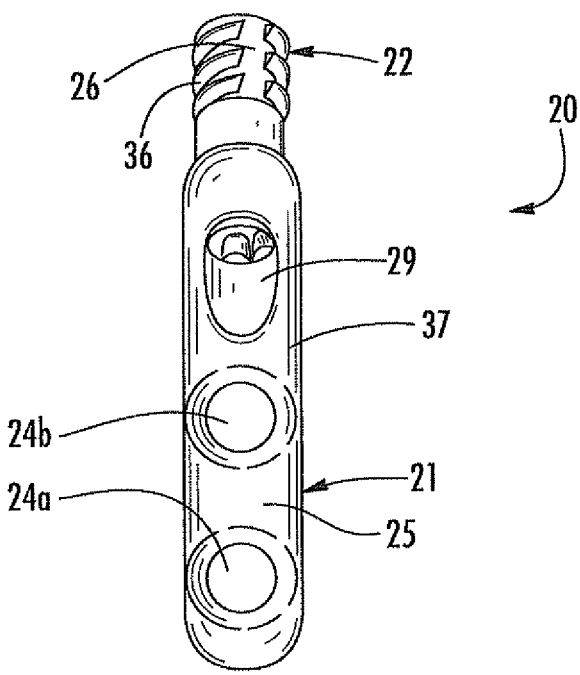
FIG. 3 is a top plan view of the arthrodesis implant of FIG. 1.
Figure 4:
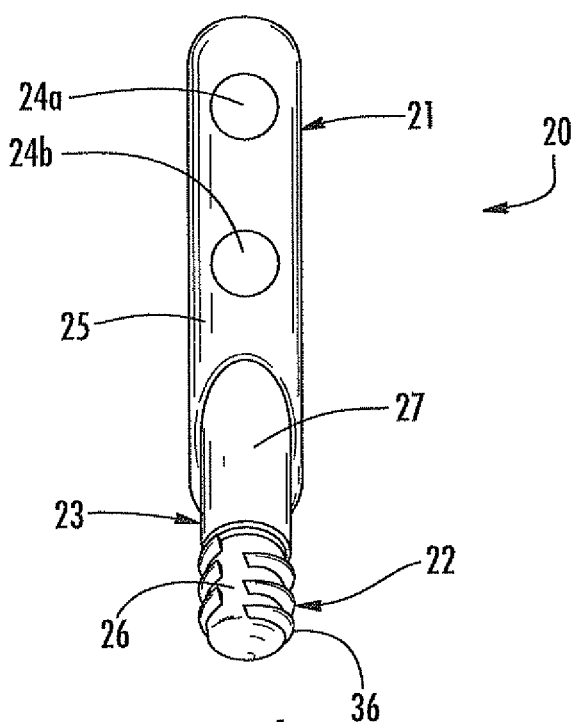
FIG. 4 is a bottom plan view of the arthrodesis implant of FIG. 1.
Figure 5:
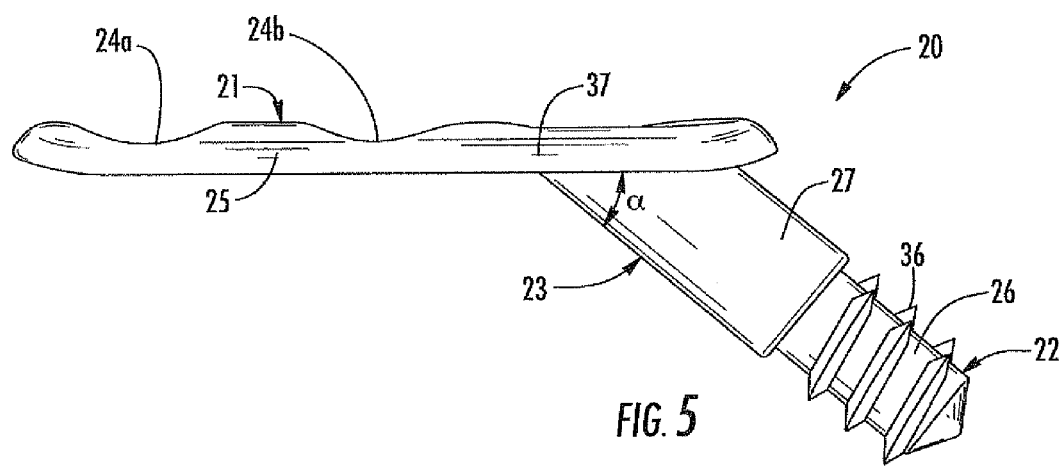
FIG. 5 is a side elevational view of the arthrodesis implant of FIG. 1.
Figure 6:
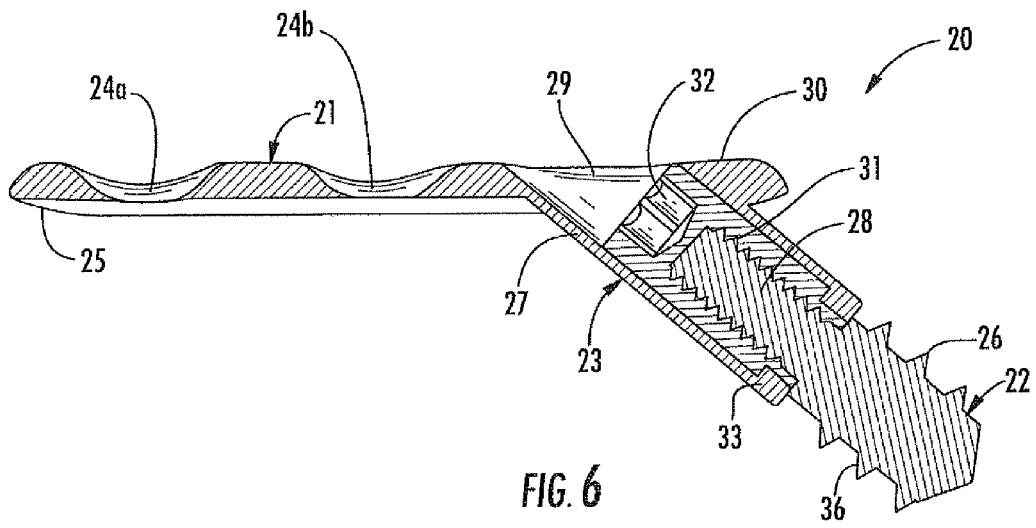
FIG. 6 is a side cross-sectional view of the arthrodesis implant of FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and completer and will fully convey the scope of the invention to those skilled in the art. Like numbers refer to like elements throughout.

Referring to FIGS. 1-12, an arthrodesis implant 20 for a finger joint of a hand of a patient is now described. As will be appreciated by those skilled in the art, the finger joint may comprise, for example, a proximal interphalangeal (PIP) joint, as defined by the coupling of the proximal and middle phalanges, or a metacarpophalangeal (MCP) joint, as defined by the coupling of the metacarpal bones and the proximal phalanges. The arthrodesis implant 20 may provide arthrodesis (fusion) between the adjacent bones in the finger joint of the patient.

As will be appreciated by those skilled in the art, the arthrodesis implant 20 is a motion-limiting or motion-eliminating type implant. The arthrodesis implant 20 may be used to treat the development of articular cartilage destruction, loss, or compromise due to Osteoarthritis or inflammatory arthritis in either the PIP joint or the MCP joint of the patient. Nonetheless, and as will be appreciated by those skilled in the art, the arthrodesis implant 20 may be used to treat other conditions were arthrodesis surgery is desirable, for example, post traumatic arthritis, arthritis associated with other inflammatory conditions, selected deformities, etc.

The arthrodesis implant 20 illustratively includes an extramedullary proximal anchor 21 comprising a first member 25 having a plurality of fastener-receiving passageways 24a-24b therethrough. The fastener-receiving passageways 24a-24b receive fasteners, for example, surgical screws to anchor the first member 25 to an extramedullary portion of a proximal bone, for example, the metacarpal bone (MCP arthrodesis) or the proximal phalanx bone (PIP arthrodesis), of the finger joint of the hand of the patient. The arthrodesis implant 20 illustratively includes an intramedullary distal anchor 22 comprising a second member 26 for being anchored within an intramedullary portion, i.e. the intramedullary canal, of a distal bone, for example, the proximal phalanx bone (MCP arthrodesis) or the middle phalanx bone (PIP arthrodesis), of the finger joint of the hand of the patient.

The first member 25 illustratively includes an elongate curved body, but could comprise a near flat plate in other embodiments not shown. Furthermore, the elongate curved body has rounded corner portions 37 to minimize local soft tissue irritation or abrasion. As will be appreciated by those skilled in the art, the low profile of the elongate curved body will increase patient comfort subsequent to implantation.

The arthrodesis implant 20 illustratively includes a coupling 23 for securing the first 25 and second 26 members together. The coupling 23 illustratively includes a tube (barrel) 27 connected to the first member 25 and extending transversely therefrom, and a fastening arrangement 30 within the tube for securing the first and second 26 members together while providing desirable coaptation and compressive forces to stimulate healing, or in this case, fusion between the proximal and distal bones of the finger joint. The tube 27 extends from the first member 25 at selected angles desired for the finger joint at the time of eventual arthrodesis. Advantageously, the tube 27 is integrally formed with the first member 25, which provides a mechanically robust arrangement.

The tube 27 illustratively extends transversely, i.e. at selected angles, from the first elongate member 25 at an angle α (FIG. 5) in a range of 20 to 90 degrees, for example, about 40 degrees, as shown in the illustrated embodiment. As will be appreciated by those skilled in the art, the transverse angle may vary based upon which PIP/MCP joint receives the arthrodesis implant 20, i.e. the index, long, ring, and small rays of the patient's hand, or may vary based upon the desired position of the joint of the finger. Advantageously, the arthrodesis implant 20 may be readily manufactured for a variety of anatomical applications.

Figure 9:
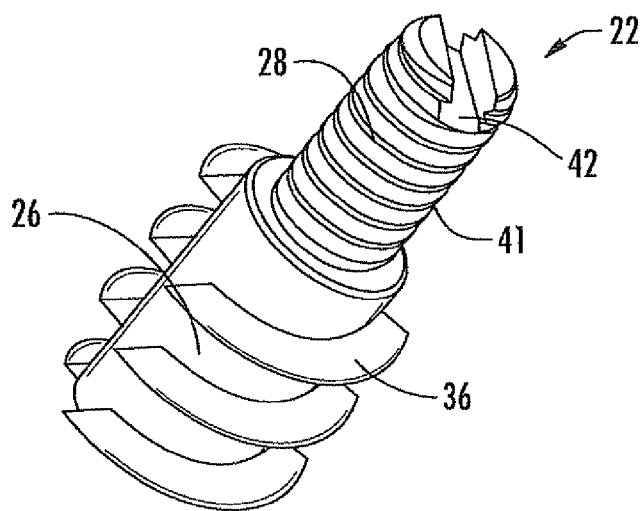
FIG. 9 is a perspective view of the intramedullary distal anchor of the arthrodesis implant of FIG. 1.
Figure 10:
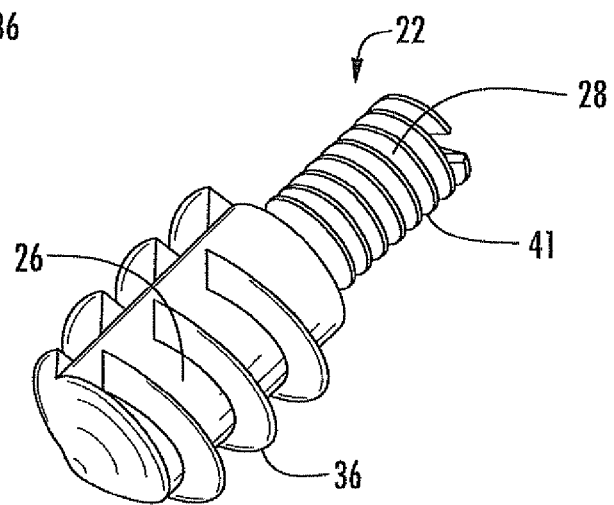
FIG. 10 is another perspective view of the intramedullary distal anchor of FIG. 9.
Figure 11:
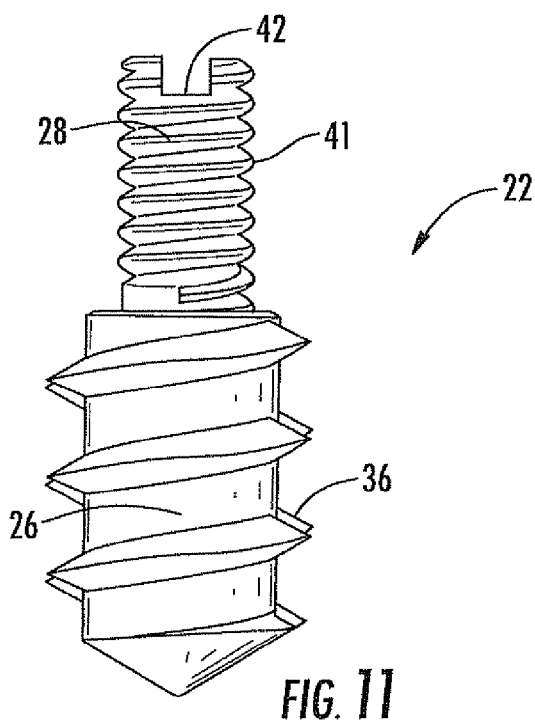
FIG. 11 is a side elevational view of the intramedullary distal anchor of FIG. 9.
Figure 12:
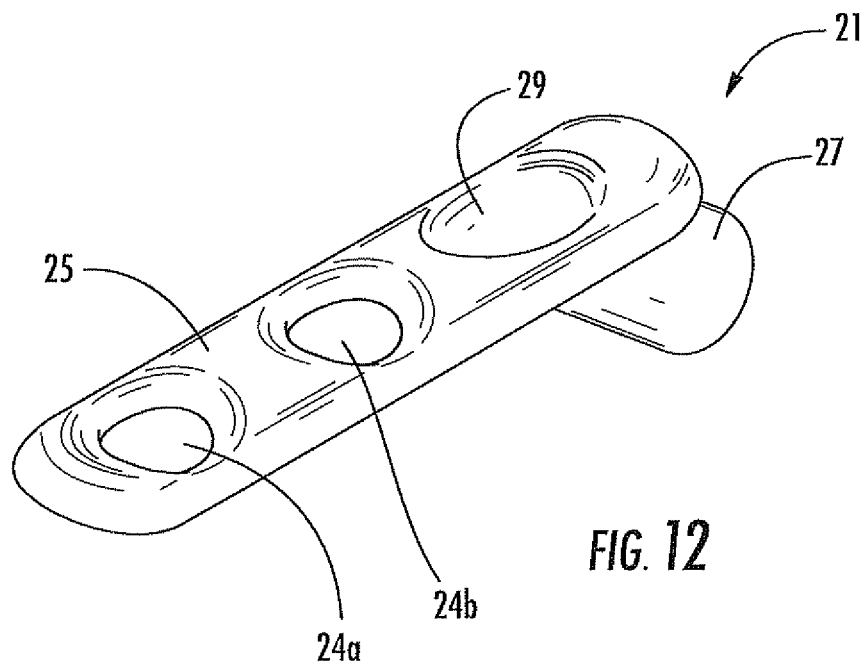
FIG. 12 is a top perspective view of the extramedullary proximal anchor of the arthrodesis implant of FIG. 1.
Figure 13:
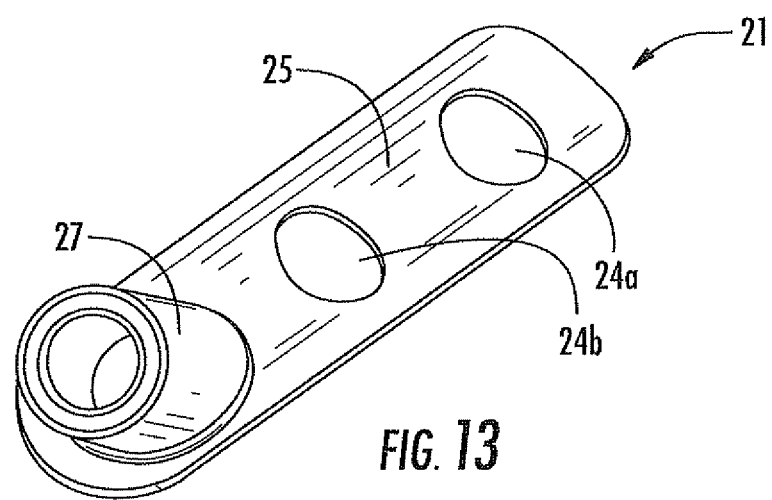
FIG. 13 is a bottom perspective view of the extramedullary proximal anchor of FIG. 12.

As perhaps best seen in FIGS. 9-11, the second member 26 illustratively includes a cylindrical body having a textured surface 36, illustratively and for example, such as the screw interface 41 depicted. As will be appreciated by those skilled in the art, the diameter of the second member 26 cylindrical body may vary to more accurately accommodate the intramedullary portion (canal) of the distal bone, i.e. the middle or proximal phalanx bones. The threaded shaft 28 extends from the second member 26. Moreover, the proximal end of the threaded shaft 28 illustratively includes a tool interface in the form of a slot 42 or mechanism known as a "sliding screw". Advantageously, the intramedullary distal anchor 22 is readily implanted into a medullary cavity of the distal bone of the patient using a surgical hand tool applied to the tool interface 42.

Figure 7:
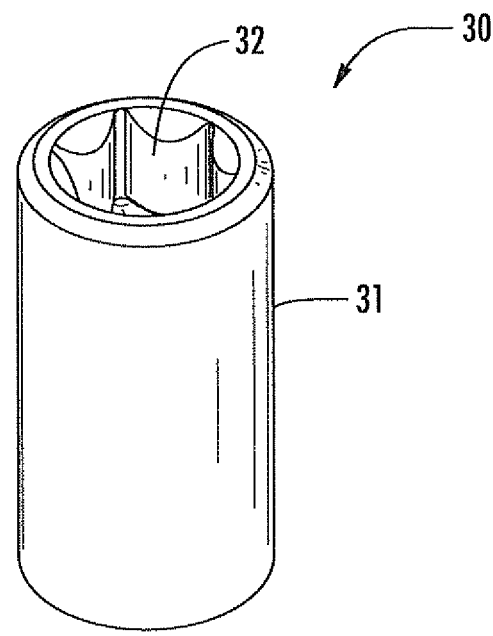
FIG. 7 is a top perspective view of the threaded sleeve of the arthrodesis implant of FIG. 1.
Figure 8:
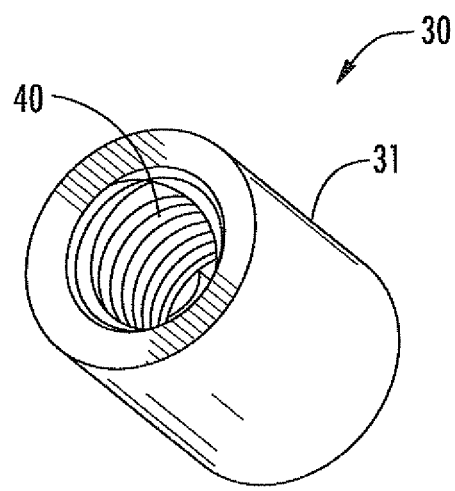
FIG. 8 is a bottom perspective view of the threaded sleeve of FIG. 7.

As perhaps best seen in FIGS. 7-8, the fastening arrangement 30 illustratively includes a threaded sleeve 31 to receive the threaded shaft 28 coupled to the intramedullary distal anchor 22. The fastening arrangement 30 also illustratively includes a tool engaging head 32 connected to the threaded sleeve 31. The tube 27 illustratively includes an internal reduced diameter portion 33 defining a stop for the threaded sleeve 31.

After implantation of the intramedullary distal anchor 22, the tube 27 is fit over the threaded shaft 28. The threaded sleeve 31 is slipped through a sleeve opening 29 in the first member 25 and then threadingly engaged with the threaded shaft 28 until it abuts the internal reduced diameter portion 33. Advantageously, this provides for a mechanically robust coupling of the intramedullary distal anchor 22 and the extramedullary proximal anchor 21 to promote coaptation or compression, known to be advantageous in affecting the successful fusion of the finger (PIP/MCP) joint of the finger.

Another aspect is directed to a method for making an arthrodesis implant 20 for a finger joint of a hand of a patient. The method may include forming an extramedullary proximal anchor 21 comprising a first member 25 having at least one fastener-receiving passageway 24a-24b therethrough to receive at least one fastener to anchor the first member to an extramedullary portion of a proximal bone of the finger joint of the hand of the patient. The method may also include forming an intramedullary distal anchor 22 comprising a second member 26 for being anchored within an intramedullary portion of a distal bone of the finger joint of the hand of the patient, and providing a coupling 23 for securing the first 25 and second members together.

Another aspect is directed to a method of implanting an arthrodesis implant 20 for a finger joint of a hand of a patient. The method may include providing the arthrodesis implant 20. The arthrodesis implant 20 may include an extramedullary proximal anchor 21 comprising a first member 25 having at least one fastener-receiving passageway 24a-24b therethrough to receive at least one fastener to anchor the first member to an extramedullary portion of a proximal bone of the finger joint of the hand of the patient, an intramedullary distal anchor 22 comprising a second member 26 for being anchored within an intramedullary portion of a distal bone of the finger joint of the hand of the patient, and a coupling 23 for securing the first and second members together.

The method may also include implanting the extramedullary proximal anchor 21 into the proximal bone, and implanting the intramedullary distal anchor 22 into the distal bone, and securing the extramedullary proximal anchor together with the intramedullary distal anchor with the coupling 23.

Other features relating to implants are disclosed in co-pending applications "MODULAR BONE FIXATION DEVICE FOR TREATMENT OF FRACTURES AND RELATED METHODS", Ser. No. 12/203,221; "ARTHROPLASTIC IMPLANT WITH SHIELD FOR BASILAR JOINT AND RELATED METHODS", Ser. No. 12/203,223; and "ARTHROPLASTIC IMPLANT WITH ANCHOR PEG FOR BASILAR JOINT AND RELATED METHODS", Ser. No. 12/203,259, all incorporated herein by reference in their entirety.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An arthrodesis implant for a finger joint of a hand of a patient comprising:

an extramedullary proximal anchor comprising a first member having at least one fastener-receiving passageway extending entirely therethrough to receive at least one fastener to anchor said first member to an extramedullary portion of a proximal bone of the finger joint of the hand of the patient;

an intramedullary distal anchor comprising a second member including a threaded shaft for being anchored within an intramedullary portion of a distal bone of the finger joint of the hand of the patient;

a coupling for securing said first and second members together, said coupling formed from a tube connected to said first member and extending transversely therefrom; and a threaded sleeve that extends into said tube and threadably receives said threaded shaft of said second member for securing said first and second members together, said threaded sleeve being positioned between said threaded shaft and said tube, said second member engaging said coupling to prevent relative movement between the second member and the coupling.

2. The arthrodesis implant according to claim 1, wherein said threaded sleeve includes a tool engaging head.

3. The arthrodesis implant according to claim 2 wherein an end of said tube spaced from said first member has an internal reduced diameter portion defining a stop for engagement by said threaded sleeve and second member to prevent all relative longitudinal movement between said threaded sleeve and said tube.

4. The arthrodesis implant according to claim 1 wherein said tube extends transversely from said first member at an angle in a range of 20 to 90 degrees.

5. The arthrodesis implant according to claim 1 wherein said first member comprises an elongate curved body.

6. The arthrodesis implant according to claim 5 wherein said elongate curved body has rounded corner portions.

7. The arthrodesis implant according to claim 1 wherein said second member comprises a cylindrical body having a textured surface.

8. The arthrodesis implant according to claim 1 wherein each fastener-receiving passageway extends straight through the entire first member.

9. The arthrodesis implant according to claim 1 wherein the first member is substantially planar.

10. The arthrodesis implant according to claim 1 wherein the fastening arrangement prevents all relative movement between the first and second members.

11. The arthrodesis implant according to claim 1 wherein the first member is free of threads.

12. The arthrodesis implant according to claim 1 wherein the fastening arrangement extends along the direction of extension of the coupling.

13. The arthrodesis implant according to claim 1 wherein an end of the tube spaced from the first member has an internal reduced diameter portion, the sleeve and the second member engaging oppositely facing surfaces of the reduced diameter portion to prevent all longitudinal movement of the sleeve and second member relative to the coupling.

14. The arthrodesis implant according to claim 13, wherein the oppositely facing surfaces of the reduced diameter portion face directions that extend parallel to the longitudinal direction of the coupling.

15. An arthrodesis implant for a finger joint of a hand of a patient comprising:

an extramedullary proximal anchor comprising a first elongate curved member having at least one fastener-receiving passageway therethrough to receive at least one fastener to anchor said first elongate curved member to an extramedullary portion of a proximal bone of the finger joint of the hand of the patient;

an intramedullary distal anchor comprising a second member that includes a threaded shaft for being anchored within an intramedullary portion of a distal bone of the finger joint of the hand of the patient;

a coupling comprising a tube connected to said first elongate curved member and extending transversely therefrom, and a threaded sleeve that extends into said tube and threadably receives said threaded shaft of said second member for securing said first elongate curved member and said second member together, said threaded sleeve being positioned between said threaded shaft and said tube, said second member engaging said coupling to prevent relative movement between the second member and the coupling.

16. The arthrodesis implant according to claim 15 wherein said threaded sleeve includes a tool engaging head.

17. The arthrodesis implant according to claim 16 wherein an end of said tube spaced from said first member has an internal reduced diameter portion defining a stop for engagement by said threaded sleeve and second member to prevent all relative longitudinal movement between said threaded sleeve and said tube.

18. The arthrodesis implant according to claim 15 wherein said tube extends transversely from said first elongate curved member at an angle in a range of 20 to 90 degrees.

19. The arthrodesis implant according to claim 15 wherein said second member comprises a cylindrical body having a textured surface.

20. The arthrodesis implant according to claim 15 wherein each fastener-receiving passageway extends straight through the entire first member.

21. The arthrodesis implant according to claim 15 wherein the first member is substantially planar.

22. The arthrodesis implant according to claim 15 wherein the fastening arrangement prevents all relative movement between the first and second members.

23. The arthrodesis implant according to claim 15 wherein the first member is free of threads.

24. The arthrodesis implant according to claim 15 wherein the fastening arrangement extends along the direction of extension of the coupling.

25. The arthrodesis implant according to claim 15 wherein an end of the tube spaced from the first member has an internal reduced diameter portion, the sleeve and the second member engaging oppositely facing surfaces of the reduced diameter portion to prevent all longitudinal movement of the sleeve and second member relative to the coupling.

26. The arthrodesis implant according to claim 25, wherein the oppositely facing surfaces of the reduced diameter portion face directions that extend parallel to the longitudinal direction of the coupling.

27. An arthrodesis implant for a finger joint of a hand of a patient comprising:

a first anchor member having at least one straight passageway extending entirely therethrough, each of the at least one passageways for receiving a fastener to anchor the first member to an extramedullary portion of a proximal bone of the finger joint of the hand of the patient;

a second anchor member having a threaded shaft and for being anchored within an intramedullary portion of a distal bone of the finger joint of the hand of the patient;

a tubular coupling connected to and extending transversely from the first member, an end of the tube spaced from the first member having an internal reduced diameter portion; and a threaded sleeve that extends into the coupling and threadably receives the threaded shaft of the second member, the threaded sleeve being positioned between the threaded shaft and the coupling and engaging the reduced diameter portion of the coupling to prevent relative movement of the second member in a first direction relative to the coupling, the second member engaging the reduced diameter portion of the coupling to prevent relative movement of the second member in a second direction opposite the first direction relative to the coupling.

28. The arthodesis implant according to claim 27 wherein the sleeve and the second member engage oppositely facing surfaces of the reduced diameter portion to prevent all longitudinal movement of the sleeve and second member relative to the coupling.

29. The arthrodesis implant according to claim 28, wherein the oppositely facing surfaces of the reduced diameter portion face directions that extend parallel to the longitudinal direction of the coupling.

* * * * *